«12» United States Patent
Jansen et al.

(10) Patent No.: US 6,858,013 B1
(45) Date of Patent: Feb. 22, 2005

(54) METHOD AND APPARATUS FOR DETERMINING THE CARDIAC OUTPUT OF A PATIENT

(76) Inventors: Jozef Reinier Cornelis Jansen, Aster 8, NL-2211 MZ, Noordwijkerhout (NL); Johannes Jacobus Schreuder, Via Eleanora Duse 32, I-21100, Varese (IT)

( * ) Notice: Subject to any disclaimer, the term of this patent is extended or adjusted under 35 U.S.C. 154(b) by 0 days.

(21) Appl. No.: 09/913,597
(22) PCT Filed: Feb. 17, 2000
(86) PCT No.: PCT/NL00/00102
§ 371 (c)(1),
(2), (4) Date: Aug. 16, 2001
(87) PCT Pub. No.: WO00/53087
PCT Pub. Date: Sep. 14, 2000

(30) Foreign Application Priority Data

Feb. 18, 1999 (NL) .............................................. 1011339

(51) Int. Cl.⁷ ................................................ A61B 5/02
(52) U.S. Cl. ....................................................... 600/526
(58) Field of Search .................................. 600/505, 526

(56) References Cited

U.S. PATENT DOCUMENTS

| 4,595,015 | A | * | 6/1986 | Jansen et al. ................ 600/526 |
| 4,819,655 | A |   | 4/1989 | Webler |
| 5,743,267 | A | * | 4/1998 | Nikolic et al. .............. 600/483 |
| 5,797,398 | A | * | 8/1998 | Bowman ..................... 600/505 |

* cited by examiner

*Primary Examiner*—Mark Bockelman
(74) *Attorney, Agent, or Firm*—Knoble Yoshida & Dunleavy, LLC

(57) ABSTRACT

In order to determine the cardiac output of a patient, the patient's respiration cycle is determined and an indicator is injected into the patient's bloodstream over a period of at least substantially one respiration cycle. The change in the indicator value in the bloodstream downstream of the injection point is measured over a period of a number (n) of respiration cycles and the injected amount of indicator is established. The cardiac output is determined on the basis of the measured change in the indicator value, the injected amount of indicator blood and the initial value thereof. To this end a first variation in the indicator value is measured over at least substantially the period of one respiration cycle, directly prior to the injection, and the change in the indicator value caused by the injection is determined on the basis of the difference between the measured change in the indicator value measured over a period of n times that of the first variation and n times the measured first variation.

9 Claims, 3 Drawing Sheets

METHOD AND APPARATUS FOR DETERMINING THE CARDIAC OUTPUT OF A PATIENT

The invention relates to a method for determining the cardiac output of a patient, wherein the patient's respiration cycle is determined and an indicator is injected into the patient's bloodstream over a period of at least substantially one respiration cycle, wherein the change in the indicator value in the bloodstream downstream of the injection point is measured over a period of a number (n) of respiration cycles and the injected amount of indicator is established, wherein the cardiac output is determined on the basis of the measured change in the indicator value, the amount of indicator injected into the blood and the initial value thereof, as well as to an apparatus for determining the cardiac output of the patient.

The measurement carried out in accordance with this method is known as thermal dilution measurement, wherein a catheter is introduced into the patient's bloodstream, via which catheter a relatively cold fluid, for example, is injected into the blood as the indicator. A sensor is attached to the catheter in question or to a similar catheter downstream of the injection point, seen in the direction of flow of the blood, by means of which the blood temperature can be measured. In this manner a so-called thermal dilution curve can be determined, which indicates the change in the temperature. Since the injected amount of indicator is known, it is possible to determine the cardiac output on the basis of the thermal dilution curve. One requirement of the prior art method is that the cardiac output be constant. In practice it has become apparent, however, that two major disruptions of the supposedly constant cardiac output exist; one factor is the pulsating output caused by the action of the heart, and the other factor is formed by all other low-frequency variations in the cardiac output, which are for example caused by artificial respiration of the patient. Generally, the variations in the cardiac output caused by the action of the heart are not considered to have a disruptive effect as regards the application of the thermal dilution method. When artificial respiration is being applied to a patient by means of an artificial respirator, however, the cardiac output is influenced to such an extent that it can no longer be considered to be constant but to be of a fluctuating nature. It is precisely when artificial respiration is being applied to a patient by means of an artificial respirator that it is highly desirable that the average cardiac output be determined with great accuracy, since this value constitutes one of the criteria in monitoring a patient's condition. Research conducted by J. R. C. Jansen et al, among others, Intensive Care Med 1990, 16, pp. 422–425, has shown that when the cardiac output is determined by means of the thermal dilution method, the measuring results may exhibit a dispersion of 65–125% of the average.

NL-B-1 005 572 discloses a method and apparatus of the above kind by means of which the accuracy of the thermal dilution method can be enhanced by injecting the indicator exactly over the period of one respiration cycle. By using only one injection over the period of one respiration cycle, the same result is obtained as by computing the average on the basis of a number of thermal dilution measurements according to the conventional method, as for example described in the aforesaid article.

The object of the invention is to further improve the method and apparatus of the kind referred to in the introduction.

In order to accomplish that objective, the method according to the invention is characterized in that a first variation of the indicator value is measured over at least substantial the period of one respiration cycle, preferably directly prior to the injection, and in that the change in the indicator value caused by the injection is determined on the basis of the difference between the change in the indicator value measured over a period of n times that of the first variation and n times the measured first variation.

In this manner the accuracy of the thermal dilution method is further enhanced in that the variation in the indicator value over a period of one respiration cycle is removed from the measurement of the indicator value over a period of n respiration cycles. As a result, all cyclical variation in the indicator value is removed from the measuring result, so that only the change in the indicator value that is caused by the injection is obtained.

Preferably, a second variation in the indicator value is measured over a period of at least substantially one respiration cycle, preferably directly contiguous to the measurement of the change in the indicator value, wherein the average of the first and the second variation is determined, which average is used for determining the change in the indicator value rather than the first variation. The advantage thus obtained is that the accuracy is further enhanced and that furthermore the slow drift in the indicator value is removed from the measuring result.

According to another embodiment, a so-called pulse contour measurement is carried out as well, whereby an arterial blood pressure signal is measured. The arterial blood pressure signal is approximately proportional to the cardiac output itself, assuming that the characteristic impedance of the vascular system is constant. This requirement is not met in practice, because said characteristic impedance varies with a relatively large time constant. According to the invention an accurate measurement is made possible in that the arterial blood pressure signal is measured, wherein the values of the stroke volume and of the cardiac output over a period of one heartbeat are computed over a period corresponding to the number (n) of respiration cycles, wherein the average of the computed values is determined, and wherein a proportionality constant is computed from a comparison of the average output value thus computed and the cardiac output value determined on the basis of the change in the indicator value, after which the stroke volume and the cardiac output are multiplied by the computed proportionality constant. Thus the result of the thermal dilution measurement is used as calibration for the pulse contour measurement, as it were, after which the cardiac output can be continuously monitored without subsequent injections by means of the pulse contour measurement. The determination of the cardiac output from the change in the indicator value can be repeated periodically, if desired, by carrying out a new injection and computing the proportionality constant.

The invention also provides an apparatus for determining the cardiac output of a patient, which apparatus comprises a processing unit having a control output for controlling injection means, a first sensor for measuring the change in an indicator value in the patient's bloodstream and a second sensor for determining the patient's respiration cycle, wherein the processing unit is arranged for measuring the change in the indicator value in the bloodstream downstream of the injection point over a number (n) of respiration cycles, establishing the injected amount of indicator and determining the cardiac output on the basis of the measured change in the indicator value, the amount of indicator injected into the blood and the initial value thereof, which apparatus is according to the invention characterized in that the processing unit is arranged for measuring a first variation of the indicator value over at least substantially one respiration cycle, preferably directly prior to the injection of the indicator, and determining the change in the indicator value resulting from the injection on the basis of the difference between the measured change in the indicator value measured over a period of n times that of the first variation and n times the measured first variation.

The invention will be explained in more detail hereafter with reference to the drawing, which schematically shows an exemplary embodiment of the apparatus according to the invention.

It is noted that the term respiration cycle as used within the framework of the description and the claims is understood to mean a natural respiration cycle as well as an artificial respiration cycle. The indicator may be a cold fluid, but also any other suitable indicator, such as a saline solution or a glucose solution or a colouring agent may be used. Although a cold fluid is used as the indicator in the present embodiment, it is also possible to use another indicator, therefore.

Figure 1:
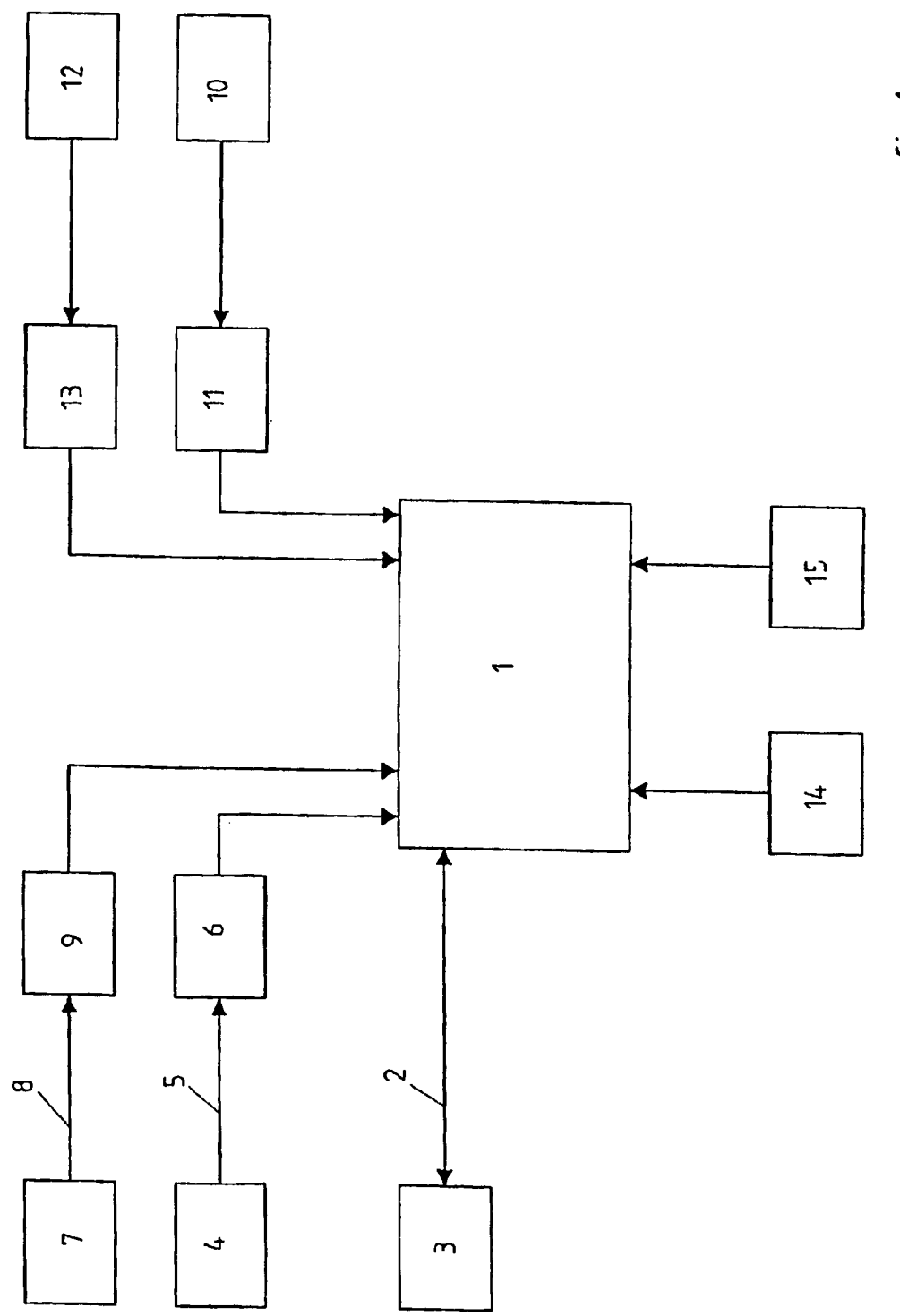
FIG. 1 is a block diagram of an embodiment of the apparatus according to the invention.

FIG. 1 shows apparatus for measuring the cardiac output of a patient, which apparatus comprises a processing unit 1, for example in the form of a PC with suitable software. The processing unit 1 comprises an input/output 2 for controlling injection means 3 (schematically indicated), by means of which a cold fluid can be injected into the patient's bloodstream. To this end a thermal dilution catheter is introduced into the patient's blood vessel in a usual manner. The temperature of said cold fluid is measured by means of a sensor 4, which is connected to processing unit 7. The catheter (not shown) is fitted with a sensor 7 located at some distance from the injection opening, by means of which the temperature of the blood downstream of the injection opening can be measured. Sensor 7 is connected to an input 8 of an amplifier 9, whose output signal is likewise supplied to the processing unit 1. Using the apparatus described so far, a so-called thermal dilution curve can be determined, from which the cardiac output can be computed on the basis of the injected amount of cold fluid and the temperature of said fluid. A plurality of injections of cold fluid would be required in order to be able to determine the average cardiac output. As is disclosed in NL-B-1 005 572, however, it is possible to determine the thermal dilution curve by means of only one injection over the period of one respiration cycle.

To this end the apparatus disclosed herein comprises a sensor 10, which is connected to processing unit 1 via an amplifier 11. Sensor 10 measures a respiration cycle-dependent signal. Such a sensor can for example measure the concentration of carbon dioxide, the strength of the air flow, the temperature of the respiration air or the like. The processing unit 1 now controls the injection means 3 in such a manner that one injection of indicator is carried out accurately for the duration of one respiration cycle and subsequently records the change in the concentration of the indicator for a number n of respiration cycles.

Figure 2:
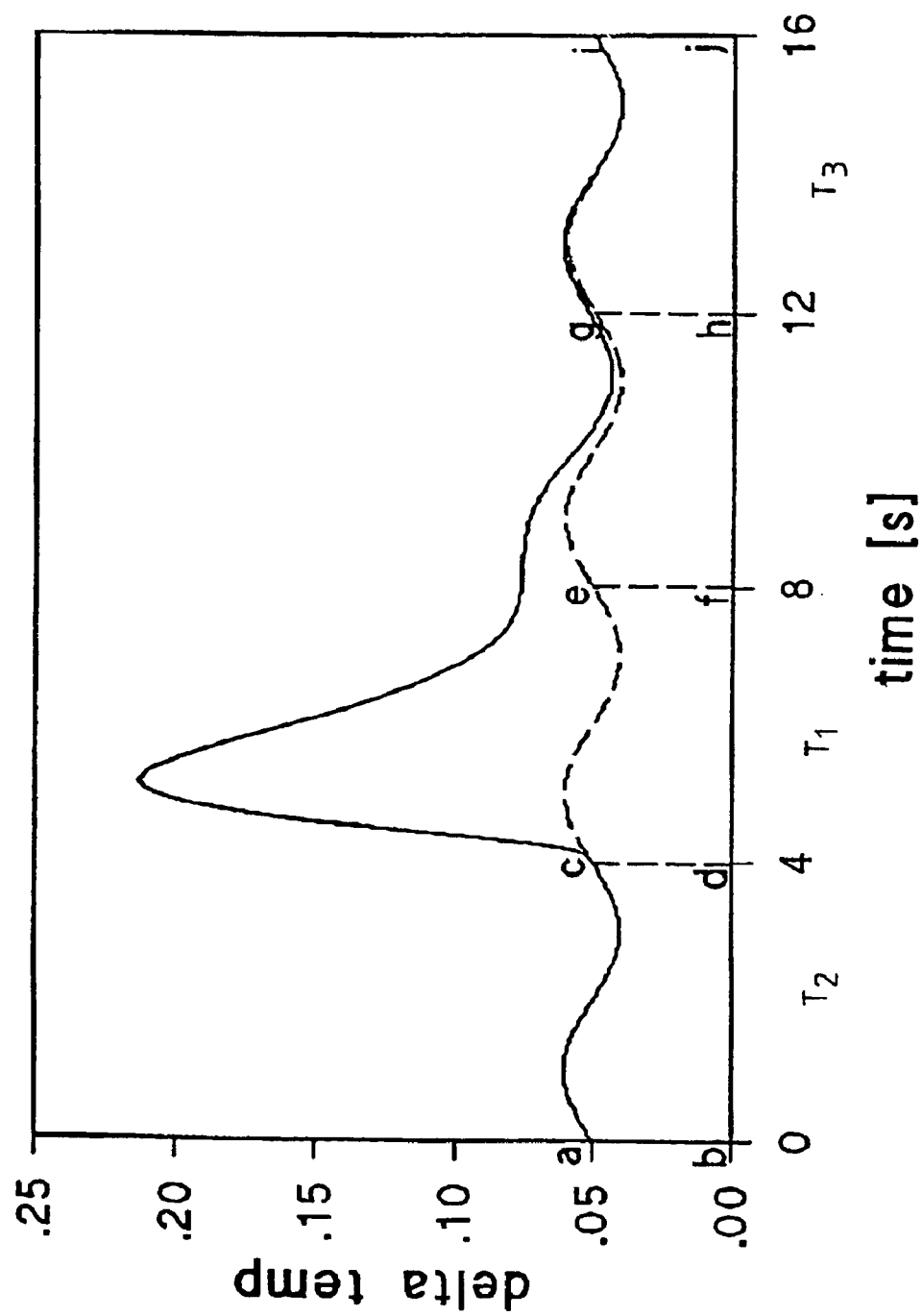
FIGS. 2 and 3 are diagrams which illustrate the method according to the invention.

FIG. 2 shows a temperature/time diagram wherein the temperature change is marked off as a function of the time. The average cardiac output is measured by one controlled injection for the duration of a respiration cycle and it is not necessary to carry out a number of measurements. In the example of FIG. 2 the period during which the change in the concentration is recorded is indicated T1. This period runs from t6=t4 to t6=12.

When a cold fluid is injected as the indicator, the following equation applies:

$$Q_i \rho_i S_i (T_b T_i) = Q'_b \rho_b S_b \int \Delta T_b(t) dt$$

wherein $Q_i$ is the injected volume, $\rho$ is the specific heat and S is the specific mass of (i) injected matter and (b) blood, respectively, T is the temperature, $Q'_b$ is the cardiac output and $\Delta T_b$ is the change in the temperature of the blood brought about by the injection of cold fluid.

Rearrangement of the formula shows how the cardiac output can be computed.

$$Q'_b = Q_i \frac{\rho_i S_i (T_b T_i)}{\rho_b S_b \int \Delta T_b(t) dt}$$

This formula forms the basis for most thermal dilution "cardiac output" computers.

Research has shown that it is not possible to achieve accurate measuring results in this manner, since the pulsating cardiac output fluctuates due to the natural respiration or artificial respiration via a ventilator. This is schematically shown in FIG. 2. In this case the temperature change also includes a temperature variation which is not caused by the injection. This influence on the respiration can be removed by measuring the area below the measured temperature curve over a period of exactly one respiration cycle, preferably directly prior to the injection of the cold fluid, in the embodiment as shown in FIG. 2 injection takes place at t=4, and consequently area A defined by the points a,b,c,d is measured AM for the duration of period T2. The determination of area B under the temperature curve defined by the points c,d,g,h, is started at the time of injection t=4, and lasts over a period of a number n of respiration cycles until t=12. The area resulting from the injection of the cold fluid will then be Area–Dil=B–n×A.

The cardiac output is then computed as:

$$Q'_b = Q_t \frac{\rho_i S_i (T_b T_i)}{\rho_b S_b \text{Area} - \text{Dil}}$$

Figure 3:
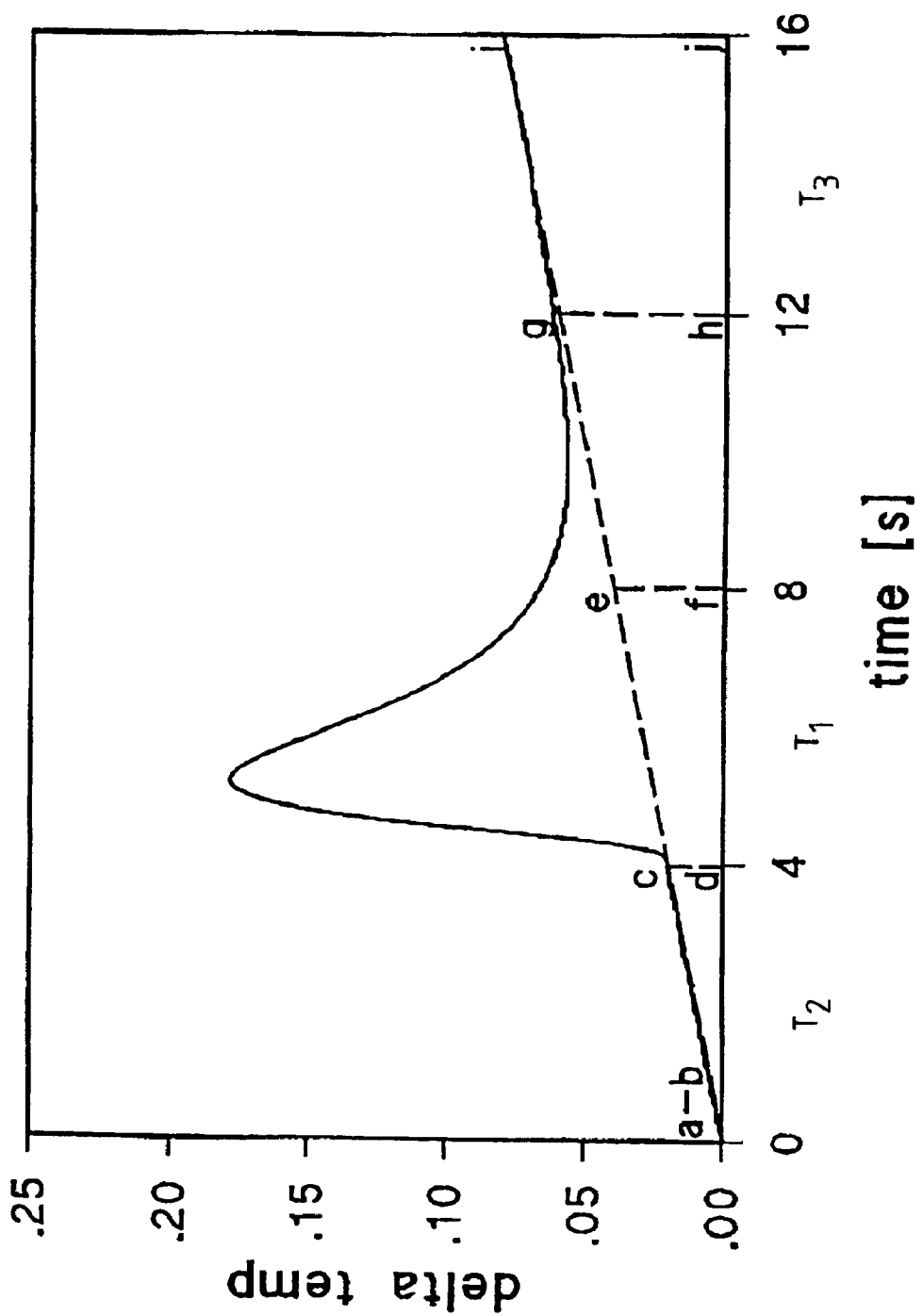

The influence of slow temperature drift resulting from an increase or decrease of the body temperature, for example, can furthermore be eliminated by measuring the temperature change over a period of exactly one respiration cycle directly prior to as well as directly contiguous to the injection. This situation is shown in FIG. 3. Both area A and area C (defined by the points g,h,i,j) are thereby measured over period T2 and over period T3, respectively, so that the area resulting from the injection of the cold fluid will then be Area–Dil=B–n/2×(A+C).

It is therefore possible with the method and apparatus disclosed herein to measure the average cardiac output of a patient with great accuracy by means of only one injection of indicator.

According to a very advantageous embodiment the apparatus is also fitted with a sensor 12, which is connected to the processing unit 1 via an amplifier 13. Sensor 12 measures the arterial blood pressure signal, for example in the aorta. It is known per se that it is possible to compute the noncalibrated value of the stroke volume and the cardiac output from said arterial blood pressure signal over a period of one pulsation of the heart. This is for example disclosed in U.S. Pat. No. 3,841,313. In the apparatus disclosed therein, the computed values of the cardiac output are recorded over the period of the measurement of the thermal dilution curve, and the average thereof is determined. Then a proportionality constant is computed by the processing unit 1 by comparing the cardiac output value thus computed with the cardiac output which has been determined by means of the thermal dilution method. Then the computed values for the stroke volume and the cardiac output resulting from the measurement of the arterial blood pressure can be continuously converted into accurate measurements by means of said proportionality constant.

If desired, the processing unit can be programmed in such a manner that a thermal dilution determination is carried out periodically in the above-described manner, and a new proportionality constant can be determined.

It is noted that the measuring results can be displayed on a screen 14, if desired. Furthermore it is noted that the thermal dilution measurement can be started automatically or by giving a suitable command, for example via a keyboard 15.

The invention is not restricted to the above-described embodiment as shown in the drawing, which can be varied in several ways without departing from the scope of the invention.

What is claimed is:

1. A method for determining a cardiac output of a patient, wherein the patient's respiration cycle is determined and an indicator is injected into the patient's bloodstream over a period of substantially one respiration cycle and an injected amount of indicator is established, wherein a change in an indicator value in the bloodstream downstream of the injection point is integrated over a measurement period ($T_1$) of a number (n) of respiration cycles, first variation in the indicator value is integrated over substantially a period ($T_2$) of one respiration cycle, prior to the injection, and a second variation in the indicator value is integrated over a period ($T_3$) of substantially one respiration cycle after the measurement period ($T_1$), wherein an average of the first and the second integrated variations is determined, and wherein the change in the indicator value caused by the injection is determined on the basis of a difference between the change in the indicator value integrated over said measurement period ($T_1$) and n times the average of the integrated first and second variations, wherein the cardiac output is determined on the basis of the thus determined change in the indicator value, an amount of indicator injected into the blood and an initial value thereof.

2. A method according to claim 1, wherein the first variation in the indicator value is measured directly prior to the injection.

3. A method according to claim 1, wherein the second variation in the indicator value is measured directly contiguous to the measurement period ($T_1$).

4. A method according to claim 1, wherein an arterial blood pressure signal is measured, wherein values of the stroke volume and of the cardiac output over a period of one heartbeat are calculated over a period corresponding to the number (n) of respiration cycles, wherein the average of the calculated values is determined, and wherein a proportionality constant is computed from a comparison of the, average output value thus calculated and the cardiac output value determined on the basis of the change in the indicator value, after which the stroke volume and the cardiac output are multiplied by the computed proportionality constant.

5. A method according to claim 4, wherein the determination of the cardiac output from the change in the indicator value is repeated periodically by carrying out a new injection and computing the proportionality constant.

6. Apparatus for deters cardiac output of a patient, which apparatus comprises a processing unit having a control output for controlling injection means, a first sensor for measuring a change in an indicator value in the patient's bloodstream and a second sensor, for determining the patient's respiration cycle, wherein the processing unit is arranged for establishing an injected amount of indicator, and for integrating a change in the indicator value in the bloodstream downstream of an injection point over a measurement period of ($T_1$) of a number (n) of respiration cycles, for integrating a first variation of the indicator value over a period ($T_2$) of substantially one respiration cycle prior to an injection, and for integrating a second variation in the indicator value over a period ($T_3$) of substantially one respiration cycle after the measurement period ($T_1$), wherein the processing unit determines an average of the first and the second integrated variations, wherein the processing unit is further arranged for determining a change in the indicator value resulting from the injection on the basis of the difference between the change in the indicator value integrated over said measurement period ($T_1$) and n times the average of the integrated first and second variations, and wherein the processing unit is arranged for determining the cardiac output on the basis of the thus determined change in the indicator value, an amount of indicator injected into the blood and an initial value thereof.

7. Apparatus according to claim 6, wherein the processing unit is arranged for measuring the first variation in the indicator value directly prior to the injection.

8. Apparatus according to claim 6, wherein the processing unit is arranged for measuring the second variation in the indicator value directly contiguous to the measurement of the change in the indicator value.

9. Apparatus according to claim 6, comprising a third sensor for measuring an arterial blood pressure signal, wherein the processing unit is arranged for calculating values of a stroke volume and of the cardiac output over a period of one heartbeat over a period corresponding to the number (n) of respiration cycles, wherein an average of the calculated values is determined, wherein the processing unit compares the average cardiac output value thus calculated and the cardiac output value determined on the basis of the change in the indicator value and computes a proportionality constant, after which the processing unit multiplies the stroke volume and the cardiac output computed from the arterial blood pressure signal by the computed proportionality constant.

* * * * *